United States Patent [19]

Yao et al.

[11] Patent Number: 4,846,950
[45] Date of Patent: Jul. 11, 1989

[54] CYCLIC CONTROLLED ELECTROLYSIS APPARATUS

[75] Inventors: Shang J. Yao; Sidney K. Wolfson, Jr., both of Pittsburgh, Pa.

[73] Assignee: Montefiore Hospital Assn of Western PA, Pittsburg, Pa.

[21] Appl. No.: 96,804

[22] Filed: Sep. 10, 1987

Related U.S. Application Data

[60] Continuation of Ser. No. 887,137, Jul. 17, 1986, which is a division of Ser. No. 530,775, Sep. 3, 1983, Pat. No. 4,663,006.

[51] Int. Cl.$^4$ ............................................. C25B 15/02
[52] U.S. Cl. .................................. 204/228; 204/231; 604/20
[58] Field of Search ................ 204/228, 231, DIG. 9; 604/29, 20

[56] References Cited

U.S. PATENT DOCUMENTS

| | | | |
|---|---|---|---|
| 3,172,083 | 3/1965 | Constantine, Jr. | 204/231 |
| 3,192,148 | 6/1965 | Chen | 204/231 |
| 3,282,834 | 11/1966 | Justi et al. | 204/182.4 |
| 3,616,412 | 10/1971 | Gnage | 204/231 |
| 4,227,988 | 10/1980 | Galney et al. | 204/231 |
| 4,326,938 | 4/1982 | Das Gupta et al. | 204/228 |

FOREIGN PATENT DOCUMENTS 7904150 5/1979 Netherlands ........................ 204/131

OTHER PUBLICATIONS

Yao et al., "Anodic Oxidation of Carbohydrates and Their Derivatives in Neutral Saline Solution", Nature, vol. 224, No. 5222, pp. 921-922, 11-29-69.
Yao et al., "Anodic Oxidation of Urea and an Electrochemical Approach to De-Ureation", Nature, vol. 241, No. 5390, pp. 471-472, 2-16-73.
Yao et al., "Controlled Electrolysis of Urea in Biological Fluids," Charge and Field Effects in Biosystems, pp. 409-412, 1984.
Yao et al., "Controlled-Potential Controlled-Current Electrolysis: In Vitro and In Vivo Electrolysis of Urea", Bioelectrochemistry and Bioenergetics, 13, (1984), pp. 15-24.
Keller et al., "Electrochemical Removal of Urea from Physiological Buffer as the Basis for a Regenerative Dialysis System", Bioelectrochem. Bioener., vol. 7, (1980), pp. 469-485.
Yao et al. (I), "Controlled Potential Electrolysis for Urea Removal in Hemodialysis: Improved Efficiency in Urea Clearance", IEEE/Frontiers of Engineering in Health Care—1982, pp. 24-27.

Primary Examiner—John F. Niebling
Assistant Examiner—Steven P. Marquis
Attorney, Agent, or Firm—Jacques M. Dulin

[57] ABSTRACT

Method and apparatus for cyclic control of both potential and current in electrolysis, called Cyclic, Controlled-potential, controlled current Electrolysis. The method can be used with a two-electrode cell (W and C), or a three-electrode set-up using a reference electrode R to form two half cells. The method involves supplying a controlled current, preferably a constant current, to the W and C electrodes to operate the electrolysis within well-defined upper and lower potential limits. In a first embodiment (called the constant-current, preset-voltage mode), when a predetermined voltage is reached, the current is reversed until a second predetermined voltage is reached. The cycle is then repeated continously. In a second embodiment (called the preset-voltage, preset-time mode) the current is maintained constant until the predetermined voltage is reached. Then the voltage is maintained constant by reducing the current until a predetermined time of operation has elapsed. Then the current is reversed and the cycle repeats. In the case of both embodiments, the cell operates as above for a preset period of time after which the preset voltage and/or cycle time control is switched with respect to W and C electrodes, the role of the electrodes thus alternating over a longer time period. By this cyclic electrolysis method, improved removal in hemodialysis or peritoneal dialysis of urea, uric acid, creatinine and other wastes is achieved. Better electrode surface regeneration, which occurs sequentially while electrolysis is continuous, is obtained. Production of undesirable or toxic substances such as chloramine, hypochlorite, nitrogen oxides, cyanide, ammonia, and the like are prevented. No electrode poisoning is observed. Both in vitro and also in vivo electrolysis is achieved by the method and apparatus of the invention. Physiologic electrolyte balance can be maintained.

20 Claims, 3 Drawing Sheets

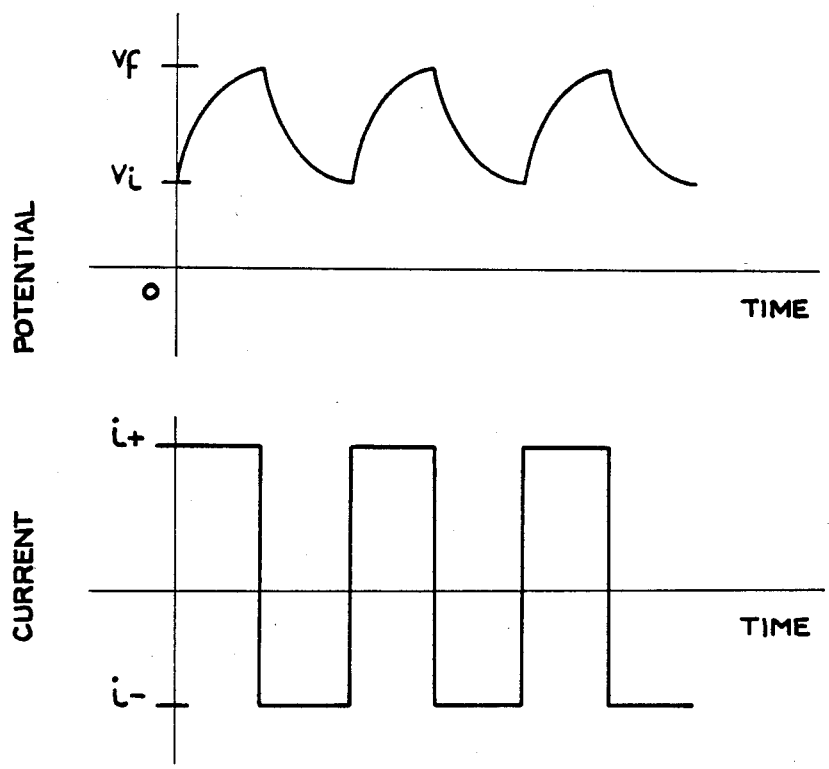
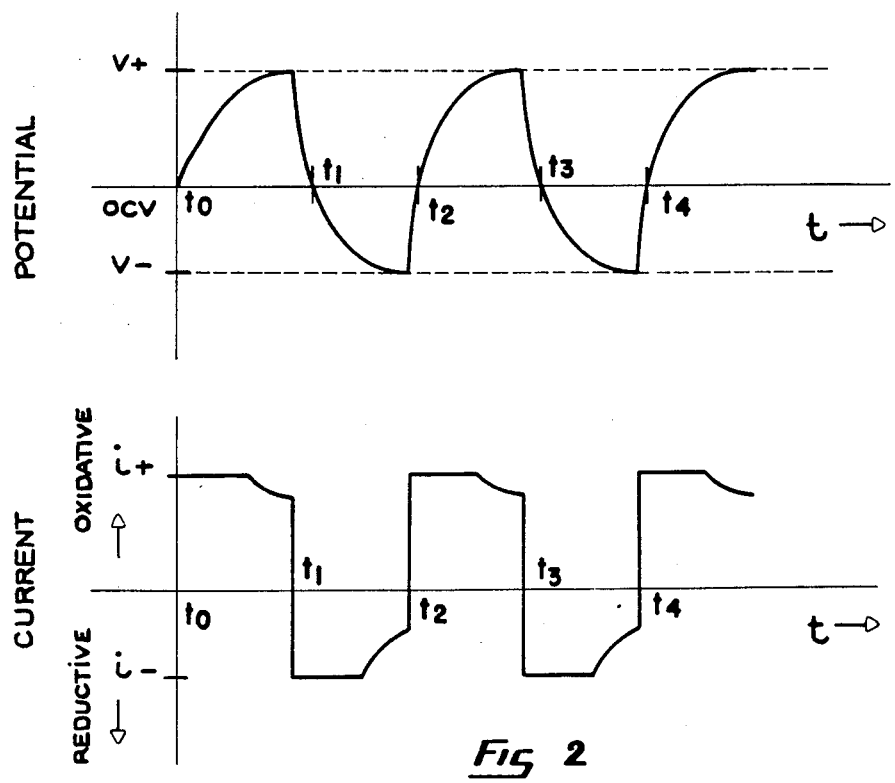

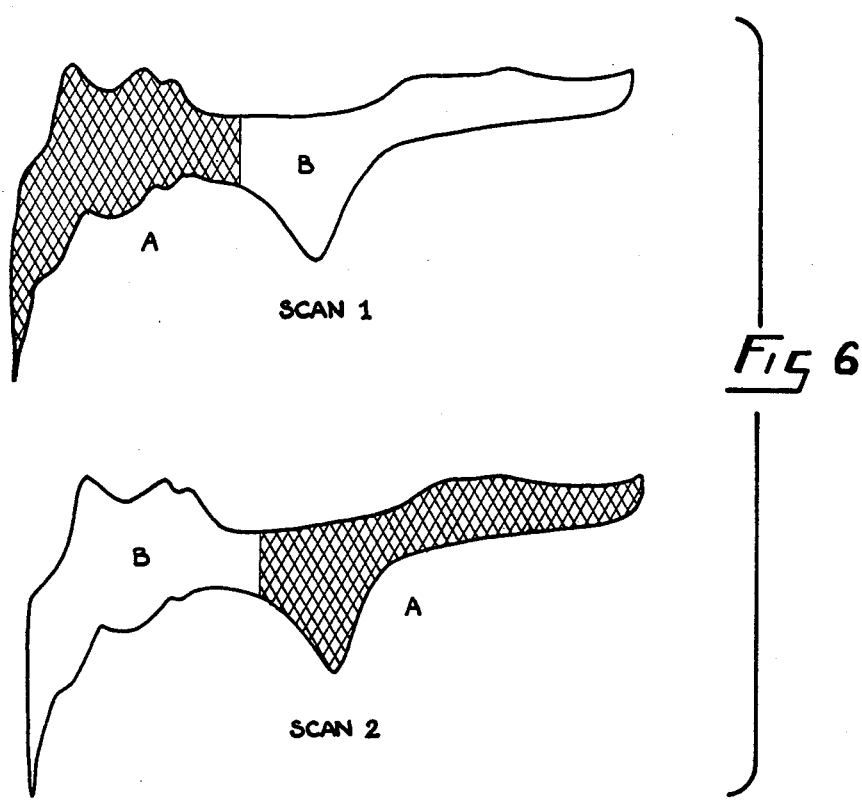
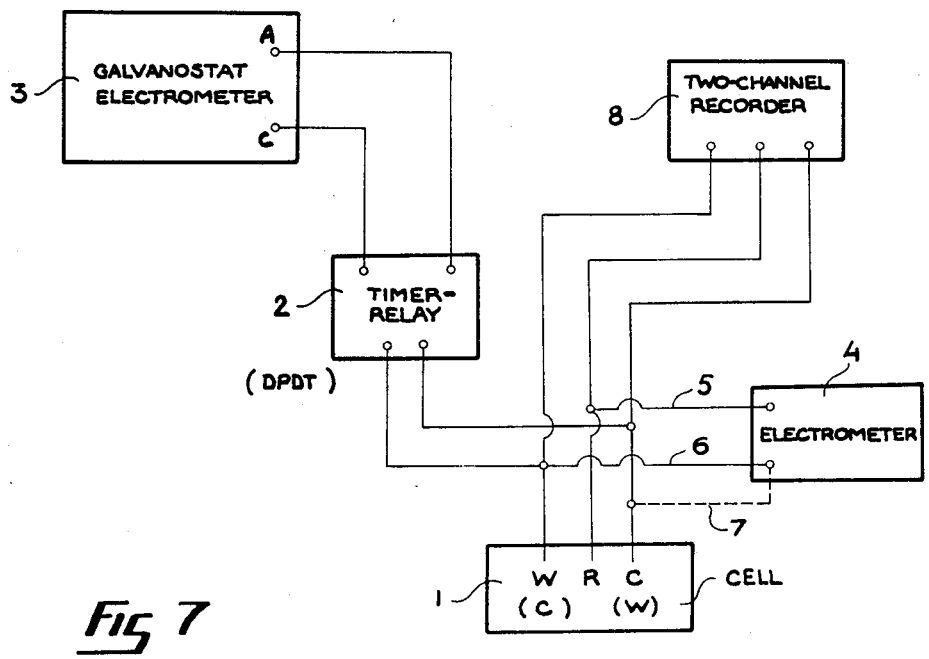

CYCLIC CONTROLLED ELECTROLYSIS APPARATUS

This is a file wrapper continuation of Ser. No. 887,137, filed July 17, 1986, which is a division of application Ser. No. 530,775 filed Sept. 3, 1983 by us for Cyclic Controlled Electrolysis now U.S. Pat. No. 4,663,006 issued May 5, 1987.

FIELD

The invention relates to apparatus and processes for Cyclic, Controlled potential, controlled current Electrolysis (CCE) employing a galvanostat (with or without a reference electrode) to monitor the potential difference between working and counter electrodes and alternately switch the current polarity so that predetermined current values i− and i+ are imposed when preset voltages, or, alternatively, voltage and time values are reached. More particularly, apparatus and process are useful in biomedical electrolysis applications, such as for removal in hemodialysis or peritoneal dialysis of urea, uric acid, creatinine, and other toxic wastes.

BACKGROUND

A growing number of patients suffering from end stage renal disease are now able to survive through the use of hemodialysis and peritoneal dialysis. While hemodialysis provides life itself for these individuals, it also obligates them to a very dependent life style. Hemodialysis, generally performed at established dialysis centers, disrupts normal work schedules and severely limits travel. It may also produce a psychological burden for the patient who is time-restricted and immobilized in a center. These patients could obviously have a more pleasant, free, and productive life if treatment at home and/or office were available. The development of a portable or wearable regenerative hemodialysis system would certainly enhance the chance of home or office dialysis. Major efforts have been directed toward the development of a portable system.

Most of the proposed portable systems are based on "closed-loop" dialysis which involves regeneration of a small volume of dialysis fluid by continuously removing the dialyzed wastes. Although a large number of toxins and wastes may be removed by passage through a charcoal bed, urea, a major metabolic waste removed by dialysis, is very poorly absorbed onto charcoal. The use of one regenerative dialysis system, Sorbsystem, has demonstrated that a urea removal device and an activated charcoal bed can provide the basis for a "closed-loop" dialysis. Sorbsystem has several problems peculiar to its urea removal method: (1) the generation of toxic ammonia; (2) the instability of the enzyme, urease, used therein; (3) the limited availability of the zirconium resins used therein; and (4) the removal of essential cations which generates an ionic imbalance.

Other approaches based on the concept of electrochemical urea removal have been explored. An indirect method, Schuenemann B., Quellhorst E., Kaiser H., Richter G., Munt K., Weidlich E., Loeffler G., Zachoriae M., Schunk O. Trans Amer. Soc. Artif. Intern Organs 1982;28:49–53, electrolyzes the chloride in the dialysate to form hypochlorite and then allows the hypochlorite to chemically react with urea to form nitrogen, carbon dioxide, and water. We believe that the presence of any hypochlorite in the dialysate is unsafe for a clinical device. Hypochlorite causes hemolysis, and can react with amines to form toxic chloramines; See Ackerman RA, Coles JS. Dialysis and Transplantation 1982;11:976–977; AAMI-ASAIO Standard for hemodialysis system. 1980; (draft), Arlington, VA. At high concentration levels, hypochlorite can disrupt the cellulosic type dialysis membranes.

The earliest and simplest method for electrochemical decomposition, degradation, displacement, synthesis, etc., processes is constant current electrolysis. In this method of electrolysis, a constant magnitude of current is supplied to the electrolysis cell from a DC (direct current) power source instrument. Electrons are generated from the oxidation of chemicals at the anode where positive ions are produced. These electrons are driven or propelled by the power supply to the cathode where reduction of chemicals occurs producing negatively charged ions. The electrical circuit is then completed by the migration of the negatively charged ions toward the anode. In accordance with the principle of electroneutrality, postive ions generated from the anodic oxidation migrate toward the cathode. The amount of electricity (coulombs) consumed is simply the constant current multiplied by the time of electrolysis.

In such a constant current system, the whole cell voltage, i.e., the potential difference between the anode and the cathode, increases as the concentration of the substances being electrolyzed decreases. Different substances are electrolyzed at different potentials. Since, in this constant current electrolysis method, potential is not controlled, different electrochemical reactions may occur simultaneously. Accordingly, different substances, many undesirable, are produced. Unless a sufficiently high concentration of the desired substance is maintained, the products and the rate of electrolysis of this specific substance are unpredictable.

A more elaborate approach is controlled potential electrolysis. This method is now well-established in both analytical chemistry and industrial processes; see: H. Lund and P. Inversen, Practical Problems in Electrolysis, in Organic Electrochemistry—An Introduction and Guide, edited by M. M. Baizer, Marcel Dekker, Inc., N.Y., 1973, Chapter IV, pp. 165–249. This method of electrolysis requires three electrodes and a potentiostat. The three electrodes are the working electrode (W), the counter or auxiliary electrode (C) and the reference electrode (R). The working electrode potential, with respect to the reference electrode, is externally controlled by the potentiostat. Current is generated by a power supply in response to the oxidation or reduction of electroactive substances at W in order to satisfy the specified voltage difference (between W and R) enforced by the potentiostat. See Keller, R. W., Jr., Brown, J. M., Wolfson, S. K., Jr., Yao, S. J., "Intermittent Potential Reversal Electrolysis for Urea Removal in Hemodialysis," reported in Proceeings IEEE/1980, Frontiers of Engineering in Health Care, 1980, 2:178–181; Yao, S. J., Brown, J. M., Wolfson, S. K., Jr., Thrivikraman, K. V., Krupper, M. A., "Controlled Potential Electrolysis for Urea Removal in Hemodialysis: Improved Efficiency in Urea Clearance," reported in Proceedings of the 4th Annual Conference IEEE/1982, Frontiers of Engineering in Health Care, Philadelphia, Pa., 1982, 4:24–27.

In this controlled potential electrolysis method, current runs from W to C. Since only one of the electrode potentials, i.e., the half cell potential with respect to the reference electrode, is under control, the potential and chemical reactions at C are unpredictable. If both electrodes (W and C) are in the same reaction mixture, different species of products may be generated at C.

We have applied the controlled potential electrolysis method to direct electrochemical oxidation of urea in Krebs-Ringer buffers and in hemodialysate solution. This has been used in conjunction with development of a new regenerative hemodializer system. See Yao, S. J., Appleby, A. J., Geisel, A., Wolfson, S. K., Jr., Ahn, B. K., Liu, C. C., "Anodic Oxidation of Urea and an Electrochemical Approach to Deureation" Nature, 1973, 241:471–472. The working electrode potential was set at +0.80 V vs Ag/AgCl by means of a potentiostat. Under these conditions the potential of the counter electrode was found to be as high as −2.0 to −2.5 V vs Ag/AgCl. The whole cell voltage, i.e., the voltage difference between W and C became 2.8 V to 3.3 V. As a result of this rather large voltage difference, some undesirable or even harmful substances could be generated as reduction products at C. One needs to be very cautious about the generation of harmful products when electrolysis is applied to clinical systems.

Urea should be safely removed at a sufficient rate to be practical. The products of the electrochemical process should contain no toxic or disruptive substances. The major products of urea oxidation should be $N_2$, $CO_2$, and water which can be easily dissipated into the air or excreted by normal respiration.

THE INVENTION

Objects

It is among the objects of the invention to provide an improved electrolysis method and apparatus that permits control of the electrochemical reactions at the electrodes to the exclusion of clinically or biochemically undesirable or harmful side products.

It is another object of the invention to provide an improved electrolysis method and apparatus that permits control of the electrolysis and improved removal of electrolyzed reactants such as urea in hemodialysis or peritoneal dialysis.

It is another object to provide an improved electrolysis method and apparatus which results in improved electrode operation, both as to reduced degradation and improved regeneration thereof.

Still further objects will be evident from the description below and figures.

FIGURES

FIG. 1 illustrates graphically both potential vs time and current vs time characteristics of a first embodiment of the invention wherein current polarity is switched when the cell voltage reaches a predetermined value;

FIG. 2 illustrates the same characteristics for a preset-voltage, preset-time embodiment of the invention;

FIG. 6 illustrates graphically the timed reversal of the working and counter electrodes pursuant to the method of the invention; and FIG. 7 illustrates diagrammatically the apparatus of the invention.

SUMMARY

Figure 3:
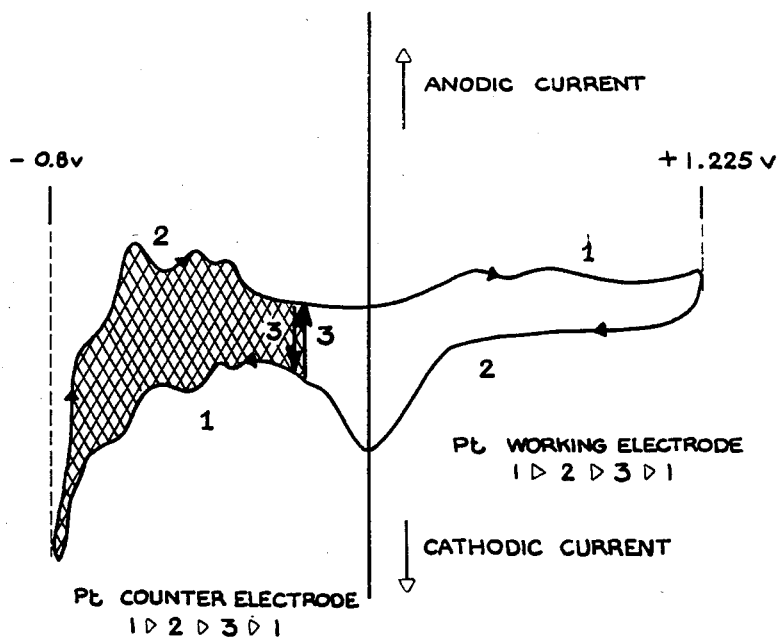
FIG. 3 illustrates graphically the cyclic voltammogram of two half cells for the embodiment of the invention where a reference electrode is used to sense the potential difference between it and the working and the counter electrodes, and shows the stepwise sequence of current vs voltage cycle.

The method and apparatus of the present invention is directed to cyclic control of both potential and current in electrolysis, called Cyclic, Controlled-potential, controlled-current Electrolysis (CCE). The method can be used with a two-electrode cell (W and C), or a three-electrode set-up using a reference electrode R to form two half cells. The method involves supplying a controlled current, preferably a constant current, to the W and C electrodes.

In a first embodiment (called the constant current, preset-voltage mode), when a predetermined voltage is reached, the current is reversed until a second predetermined voltage is reached. The cycle is then repeated continuously. In a second embodiment (called the preset-voltage, preset-time mode), the current is maintained constant until the predetermined voltage is reached. Then the voltage is maintained constant by reducing the current until a predetermined time of operation has elapsed. Then the current is reversed and the cycle repeats.

By this cyclic electrolysis method, one achieves improved removal of urea, uric acid, creatinine and other wastes in hemodialysis or peritoneal dialysis. In the case of use of the reference electrode, the invention results in better electrode surface regeneration. In all embodiments of the invention, the electrodes are regenerated sequentially while electrolysis is continuous. By careful predetermined choice of the upper bounds of oxidation potential, in terms of whole cell or half cell voltage, we prevent production of undesirable or toxic substances such as chloramine, hypochlorite, nitrogen oxides, cyanide, ammonia, and the like. Other substances, such as creatinine, are removed, and no electrode poisoning is observed. Both in vitro and in vivo electrolysis is achieved by the method and apparatus of the invention. Physiologic electrolyte balance can be maintained. Accordingly, the method and apparatus of the invention provides a significant advance in ameliorating cases of uremia.

Results of the method on recirculated canine dialysate indicate that a rate of urea removal in canine dialysate exceeding 0.9 g/m2hr has been achieved. For a 1 m2 electrode this is three times the rate of endogenuous urea production. Furthermore, the electrodes are not poisoned or damaged by any substance present in the dialysate.

DETAILED DESCRIPTION OF THE BEST MODE OF PRACTICING THE INVENTION

The present invention is directed to a method of electrolysis involving both control of potential and control of current in a cyclic mode, called Cyclic, Controlled-potential controlled-current Electrolysis (CCE). The descriptions are by way of illustration and not by way of limitation of the principles of the invention.

A positive constant current, i+ is supplied to W and C electrodes from a galvanostat. The potential difference between these two electrodes, i.e., the whole cell voltage, is preset to a predetermined limiting value. As electrolysis proceeds, the whole cell voltage increases as the concentration of the electroactive species at the electrode surfaces decreases. The whole cell voltage will also increase if the internal electrical resistance of the cell increases for some other reason. When the cell voltage increases to the preset value, the current polarity is switched so that a negative constant current, $i-$, is supplied to the cell. This $i-$ does not need to have the same absolute value as that of the original $i+$. When the cell voltage drops to a second predetermined value, the electrode current will be switched back to their original value of $i+$.

These steps result in the potential vs time and current vs time curves shown in FIG. 1. With CCE, the currents $i+$ and $i-$ are preset, and the electrolysis operates within a well-defined potential range from $Vi$ to $Vf$. The cell voltage $V = Vf - Vi$ can be predetermined by studying the cyclic voltammogram of the electroactive species reactions at the selected electrolysis electrode, and by analyzing the products of the cyclic voltammetry. Once the voltage is determined, the parameters of current, voltage and time for cyclic operation can be set.

An alternative embodiment of the CCE electrolysis of this invention is cyclic operation in a preset-voltage presettime mode. As seen in FIG. 2, the oxidative current is maintained constant until a predetermined voltage $V+$ is reached. The cell is then maintained at the preset-voltage value until a preset time $t_1$ has elapsed. The current may need to be decreased in order to keep the cell voltage at $V+$ (see FIG. 2, lower curve), or the concentration of the reactants can be controlled, e.g., by electrode separation, solution volume reduction, or removing a portion of the electrode from the solution. When the predetermined time has elapsed, the current polarity is switched from oxidative to reductive, and maintained until a predetermined lower bound voltage $V-$ is reached. The cell is maintained, as above described at $V-$ until a preset time $t_2$ has elapsed. Then the operation will automatically cyce again, i.e., $V-$, $t_2 \rightarrow V+$, $t_3 \rightarrow V-$, $t_4 \rightarrow$ . . .

The W and C electrodes can be made of either the same or different materials. When, in a special case, the same material, e.g., Pt-black, is employed for both electrodes, the polarity switching step also serves the purpose of regenerating the initial working electrode W (anode), while simultaneously utilizing the initial counter electrode C as the now-working electrode (anode). Thus, the electrolysis is continuing without disruption, while both electrodes are sequentially regenerated. Other electrode materials may be used, such as platinized titanium, rhodium black, palladium black, gold, rhodium, platinum, and palladium, or other equivalent electrode materials.

The advantages of CCE are further demonstrated in an alternate embodiment employing a reference electrode R in the cell. This R electrode is employed to read the potential difference between W and R. It can also be used to read the potential difference between C and R. The absolute sum of these two half cell instananeous voltages is the whole cell instantaneous voltage. The half cell voltage of an electrode limits the electrochemical processes which may operate in that half cell. The two half cell voltages, W vs R and C vs R, provide chemically defined values for presetting the $Vi$ and $Vf$ of the whole cell.

Figure 4:
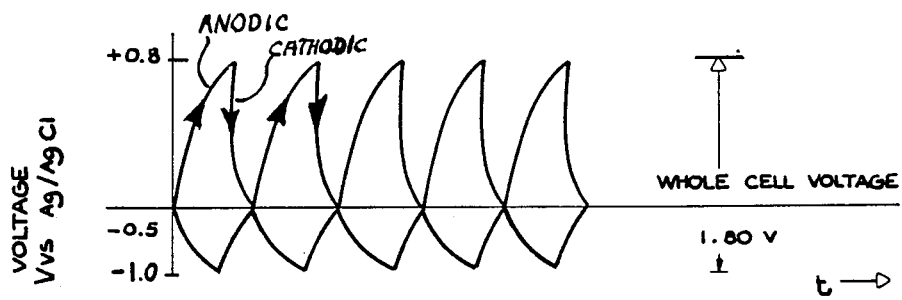
FIG. 4 illustrates graphically the voltage vs time curves for the half cells of the embodiment of FIG. 3.
Figure 5:
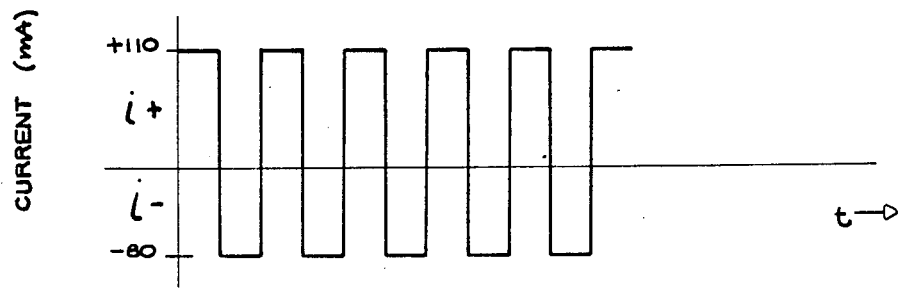
FIG. 5 illustrates graphically the current vs time curve for the half cells of the embodiment of FIG. 3.

This half-cell embodiment is illustrated in FIGS. 3-5. FIG. 3 shows a cyclic voltammogram (current vs voltage) of urea solution at Pt-black electrodes, the working electrode being to the right and the counter electrode to the left. FIG. 3 further shows the stepwise sequence of the current vs voltage cycle with the counter electrode area to the left shown in contrasting hatching. FIG. 4 shows the voltage vs time curves for the constant-current, preset-voltage method for the two half cells. The working electrode is 1.3 V (i.e., $-0.5$ V to $+0.8$ V vs. Ag/AgCl), and the counter electrode is 0.50 V (i.e., $-0.5$ V to $-1.0$ V vs. Ag/AgCl). FIG. 5 shows the corresponding current vs time curve with constant current being maintained at an $i+$ of $+110$ milliamperes, and an $i-$ of $-80$ ma.

A timer-relay (see FIG. 7) is used to reverse the current in entire operating potential region of the W and C electrodes. This provides better surface regeneration on the electrodes. This reversal process is schematically illustrated in FIG. 6. Note that the voltage/current shaded regions (areas) of scan I are reversed from those of scan II. We prefer to use as a galvanostat-electrometer Model 545 made by ECO Instruments of Boston, Mass. FIG. 7 shows the arrangement of the cell containing the electrodes hooked up to the galvanostat, and timer with current reversing switch. Particularly for in vivo work, we may use any type of implantable cell for housing the electrodes and permitting the substances to be electrolyzed into contact therewith. We prefer to use the cells shown in our U.S. Pat. Nos. 3,878,564 and 3,994,799, the disclosure of which is incorporated by reference herewith.

SPECIFIC EXAMPLES

The CCE method was applied to removal of dialysate urea, and the whole cell voltage was set to be 1.80 V (FIG. 4). The upper bound potential of W vs R was set at $+0.80$ V vs Ag/AgCl. The lower bound potential of the counter electrode was set to be $-1.00$ V vs Ag/AgCl. Thus, the operating range became C: $-0.50 \leftarrow -1.00$ and C: $-0.50 \leftarrow +0.80$. They added up to provide a maximum whole cell voltage of 1.80 V. Krebs-Ringer phosphate buffer solution with an intitial urea level of 60 mg/dl was used as the electrolyte. The rate of urea removal (urea electrolysis) was 1 g/hr to 1.5 g/hr for a 1 m$^2$ Pt-black electrode pair. Since the upper bound oxidation potential was set at $+0.80$ V vs Ag/AgCl, no hypochlorite (an undesirable product) was produced. There were no detectable toxic nitrogenous substances such as $NO_3^-$, $NO_2^-$, $CN^-$, $NH_4^+$, etc. Total Pt introduced into solution, including both dissolved Pt ions and Pt-black particles, was always negligible, being below 2 ppm as measured by atomic absorption specrophotometry. The sole gaseous substances produced, as observed from gas chromatography, were $N_2$, $CO_2$, and water vapor.

Moreover, because CCE preserves electroneutrality, physiologic electrolyte balance was maintained. The concentrations of $Na^+$, $K^+$, $Ca^{++}$, $H^+$, etc., ions remained constant throughout the controlled electrolysis. The same Pt-black electrode was used for over 15 runs for several months without any observable deterioration, or reduction in the rate of urea removal. Runs on urea removal of uremic dog recirculated hemodialysate demonstrates that these electrodes were not poisoned or degraded at all after the in vivo electrolysis. We have also found that creatinine is concurrently removed. These CCE runs using Pt-electrodes demonstrate not only that the electrochemical reactions are controlled, but also that the regeneration of electrodes can be controlled.

We have also determined in our studies of CCE a precisely defined upper boundary potential for the W electrode for the elcctrolysis of urea. It has been discovered to be $+1.25$ V vs Ag/AgCl when acetate dialysis fluid is used. Hypochlorite has not been found to be greater than 0.1 ppm in all CCE electrolysis in which the upper boundary potential of W had been preset at a +1.25 V. Urea oxidation current, as is seen from its cyclic voltammogram, was much more pronounced from +0.80 V to +1.25 than that observed below +0.80 V. $N_2$ can be strongly adsorbed on Pt-black, causing a reduction in the rate of urea oxidation. The use of an $He/O_2$: 88/12 mixture to drive off $N_2$ in the electrolyte (dialysis fluid) and that adsorbed on the electrode surface improves reaction rate. The $N_2$ may be dissolved in the electrolyte from the air, or produced at the electrode during the direct electrolysis of urea. By employing the conditions of +1.25 V as the maximum upper boundary potential and $N_2$-free electrolysis, we have achieved a rate of 2.2 g urea electrolysis/hr for a 1 $m^2$ Pt-black electrode pair in acetate dialysis fluid containing 200 mg/dl of glucose and 200 mg/dl of urea.

By way of comparison of the CCE method of this invention with uncontrolled electrolysis of urea for an artificial kidney, see M. Fels, "Recyle of Dialysate for the Artificial Kidney by Electrochemical Degradation of Waste Metabolites: Continuous Reactor Investigation," Medical & Biological Engineering & Computing, 20:257-263 (1982). In that process, an excess of $ClO^-$, $ClO_2^-$ and $ClO_3^-$ ions was produced and a pH drop of about 1 unit to 3-4 units was observed depending on the buffer used. Fels concluded that these side effects would preclude clinical application. Similar uncontrolled electrolysis was adopted for urea removal in a regenerative hemofiltration and hemodialysis system by B. Schuenemann, E. Quellhorst, H. Kaiser, G. Richter, K. Mundt, E. Weidlich, G. Loeffler, M. Zachariae and O. Schunk in "Regeneration of Filtrate and Dialysis Fluid by Electro-oxidation and Adsorption," Trans. Amer. Soc. Artif. Intern. Organs, 28:49-53 (1982). Although in the Schuenemann et al study a special cathodic reactor fixed to the electrolysis cell unit was introduced to remove remaining hypochlorite $OCl^-$ and other undesirable oxidation products, we believe that the oxychlorides could react with amines and amino acids in the dialysate to form chloramines before they were removed.

DIALYSATE ELECTROLYSIS

The method as described above was employed in in vivo tests on induced uremia in canines, with dialysate being electrolyzed in the constant current, preset-voltage mode described above.

Prior to the dialysate and electrolysis tests, a canine model for uremia had to be established. The first step was the implantation of a suitable, chronic, arteriovenous shunt for use in dialysis. A silicone rubber catheter (Dow-Corning, Midland, Mich.) was placed to connect the common carotid artery and external jugular vein and connected to an infusion "T". The area was protected by a cervical collar.

Two methods were used for uremia induction: ureteral ligation and nephrectomy. Two liters of dialysis fluid, an acetate solution, (Eri-lyte ®, 8336, 120-P, Erika, Inc.), was recirculated via a pump (Model 3500, Sarns, Inc., Ann Arbor, Mich.), at 200 ml/min, between the dialyzer and a sterile reservoir. Blood was circulated by another pump ($S_{10}K$ II Blood Pump, Sarns, Inc., Ann Arbor, Mich.), at a rate of 500 ml/min. During the dialysis, which usually lasted six hours, ureanitrogen, creatinine, uric acid, glucose, and electrolyte levels of both blood (every 30 min.) and dialysate (every 15 min.) were checked.

In the ureteral ligation test, the dialysis proceeded for five hours with hourly 50% exchanges of fresh dialysis fluid. The 5th hour spent dialysis fluid was collected for electrolysis by the constant current preset-voltage method. The dialysate level of urea-nitrogen (103 mg/dl), creatinine (6.1 mg/dl), and glucose (149 mg/dl), was considered typical of what might be encountered clinically.

In the second test, nephrectomy was employed for the induction of uremia. The methods described by Lopukhin, YuM. (trans. Aksenova, L.) *Experimental Surgery*. Moscow: Mir Publishers, 1976, pp 287-291, and Markowitz, J., Archibald, J., Downie, H. G., *Experimental Surgery*, Baltimore: The Williams & Wilkins Co., 1964, pp 479, were adapted for this test. This involved removal of one entire kidney and 4/5 of the remaining kidney. The animal thus was limited to 10% of its original renal tissue. This produced chronic uremia. Care had to be taken to preserve blood supply and urine drainage from the remaining 1/5 kidney. The nephrectomized uremic dog was ready for dialysis when its BUN reached 161 mg/dl. Dialysis and monitoring procedures were performed for the first hour and dialysate collected for electrolysis as described above. The collected dialysate had a desired urea nitrogen level of 119 mg/dl. Electrolysis was performed in the same apparatus and by the same method used in the first test.

ELECTROLYSIS TEST RESULTS

Electrolysis was carried out in a reaction vessel set-up of the type described in Yao, S. J., Brown, J. M., Wolfson, S. K. Jr., Thrivikraman, K. V., Krupper, M. A., Proceedings of the 4th Annual Conference IEEE/1982 Frontiers of Engineering in Health Care, Philadelphia, Pa. 1982; 4:24-27; and Yao, S. J., Krupper, M. A., Wolfson, S. K., Jr., Thrivikraman, K. V., Chuang, W. W., Twelfth Annual Clinical Dialysis and Transplant Forum, National Kidney Foundation 1982; Dec. 8-13:37. Platinized, perforated Pt electrodes, 125 sq cm each were employed for both the anode and cathode; a Ag/AgCl reference electrode was used to maintain +0.80 V at the anode. The dialysate was slowly recirculated via silicone tubing and pump to provide stirring. Since relatively small electrodes (125 sq cm) were used, electrolysis extended for longer than 72 hours in order to observe an appreciable and definite rate of urea removal. Table I shows the effect of electrolysis upon the concentration of several constituents of the dialysate collected from the ureteral ligation test. The rate of urea removal was 0.6 $g/m^2hr$ (urea-nitrogen: 0.27 $g/m^2hr$) It is of interest to note that creatinine, an important toxic waste, was also removed by electrolysis.

TABLE I

| Concentration Changes During Electrolysis of Dialysate - Upper Boundary +.8V. | | | |
|---|---|---|---|
| | 0 hr. | 32 hr. | 72 hr. |
| Glucose (mg/dl) | 147 | 142 | 102 |
| Urea-N (mg/dl) | 104 | 99 | 83 |
| Creatinine (mg/dl) | 6.0 | 3.3 | 0.7 |
| Uric acid (mg/dl) | 0.3 | 0.3 | 0.4 |
| Sodium (meq/l) | 135 | 136 | 138 |
| Potassium (meq/l) | 4.0 | 4.1 | 4.5 |
| Chloride (meq/l) | 107 | 111 | 113 |
| Calcium (mg/dl) | 5.4 | 5.6 | 6.0 |

TABLE I-continued
Concentration Changes During Electrolysis of Dialysate - Upper Boundary +.8V.

|  | 0 hr. | 32 hr. | 72 hr. |
|---|---|---|---|
| Phosphorus (mg/dl) | 7.3 | 7.1 | 7.2 |
| pH | 7.7 | 7.1 | 7.0 |

We have also established a standard test for performance of urea electrolysis electrodes. This involves a 6 hour run in Eri-lyte solution containing urea nitrogen 100 mg/dl. The experimental electrodes were tested in this system both before and after electrolysis of canine dialysate. A rate of urea removal of 0.9 to 1.0 g/m$^2$hr was unchanged by exposure to animal dialysate electrolysis at +0.80 V. This indicates that the electrodes were satisfactorily regenerated by the cyclic controlled electrolysis method of this invention. Moreover, the electrodes were not poisoned by any substances present in the canine dialysate. There was no observable mechanical damage to the electrodes during the prolonged recirculating electrolysis.

In vitro studies with acetate buffer indicate that when the potential of the working electrode was raised from +0.80 V to +1.20 V vs Ag/AgCl and the electrolysis system gassed with a He/O$_2$ (88:12) mixture, there is a twofold increase in the rate of urea removal without the formation of hypochlorite. Accordingly, in the second test, the dialysate from the nephrectomized dogs was electrolyzed at +1.20 V vs. Ag/AgCl with He/02 gassing in accordance with the control program previously described, Yao, S. J., Wolfson, S. K., Jr., Krupper, M. A., Wu, K. J., 1983, Proceedings Bioelectrochemistry and Bioenergetics, University of Nottingham, Abacus Press, 409-411 (1984) published as "Controlled Electrolysis of Urea in Biological Fluids," in Charge and Field Effects in Biosystems, Ed. Allen, J. J., Usherwood, P.N.R. UK (in press) 1983. Urea removal at 0.9 g/m$^2$hr was achieved (Table II). Creatinine, uric acid, and glucose are concurrently removed and ionic balance is completely maintained. The pH decreased by only one unit for the entire 138 hr. electrolysis period.

The second test showing operation close to the upper boundary potential demonstrates a substantial improvement over that of the first test. The results presented in Table II represent the present best mode of our dialysate electrolysis method. The rate of urea removal at 0.9 g/m$^2$hr is very significant. For a 1 m$^2$ electrode this is three times the rate of endogenous urea production. The reactor "cell" currently employed is a batch type vessel. We have calculated, based upon earlier experiments with a flow cell prototype, Keller, R. W., Jr., Brown, J. M., Wolfson, S. K., Jr., Yao, S. J., Proceedings IEEE/1980 Frontiers of Engineering in Health Care 1980; 2:178-181, that a much higher rate, ca 1.5-2.0 g/m$^2$hr is achievable where a flow-through reactor is used.

TABLE II
Concentration Changes During Electrolysis of Dialysate - Upper Boundary +1.20V.

|  | 0 hr. | 65 hr. | 138 hr. |
|---|---|---|---|
| Glucose (mg/dl) | 413 | 192 | 41 |
| Urea-N (mg/dl) | 119 | 90 | 56 |
| Creatinine (mg/dl) | 3.7 | 0.4 | 0.3 |
| Uric acid (mg/dl) | 0.8 | 0.2 | 0.3 |
| Sodium (meq/l) | 133 | 132 | 134 |
| Potassium (meq/l) | 3.2 | 3.2 | 3.3 |
| Chloride (meq/l) | 107 | 107 | 108 |

TABLE II-continued
Concentration Changes During Electrolysis of Dialysate - Upper Boundary +1.20V.

|  | 0 hr. | 65 hr. | 138 hr. |
|---|---|---|---|
| Calcium (mg/dl) | 6.5 | 6.4 | 6.4 |
| Phosphorus (mg/dl) | 7.2 | 7.2 | 7.2 |
| pH | 7.5 | 7.2 | 6.5 |

Moreover, in the test reported here a substantial proportion of the electrical current was diverted for the electrolysis of the glucose which was exceptionally high, 413 mg/dl initially, and was reduced (tenfold) to 41 mg/dl over a 138 hour electrolysis. One would expect the rate of canine (or human) dialysate urea removal to exceed 3 g/m$^2$hr (10 times the endogenous urea production for a 1 m$^2$ electrode), where an implantable cell of the type shown in our U.S. Patents is used, and where dialysate glucose is $\leq$150 mg/dl. This is a recommended rate for a clinical electrochemical urea removal system.

The fact that creatinine and uric acid are also removed rapidly by the method of the invention is unexpected. Because these are removed in addition to urea, there is no longer a need for an activated charcoal bed; a single electrochemical cell using the CCE method herein is sufficient for a regenerative dialyzer. Even where charcoal is employed, the CCE method may be used since charcoal does not interfere. Surprisingly, complete ionic balance was maintained, thus eliminating the need for the infusion of ions during dialysis. The pH may decrease slightly, in the batch method, but where there is electrolysis in conjunction with dialysis, the capacity of the body's buffering system should maintain pH at its physiologic level. When CCE employs much larger electrode areas, ca 1 m$^2$, the prolonged run (138 hr.) becomes unnecessary.

The apparatus set-up is shown in FIG. 7. Using cells of the types shown in our U.S. Pat. Nos. 3,818,564 and 3,994,799 with the galvanostat-electrometer, timer relay, etc., being miniaturized, the entire apparatus may be made implantable for truly continuous perambulatory dialysis. The cell 1, containing the Working W, Reference R, and Counter C electrodes, is hooked, as shown by the several leads (not numbered) through a double pole, double throw timer relay 2, and thence to the galvanostat electrometer 3. The (C) and (W) in cell 1 illustrates that the electrodes are alternately switched as called for in the CCE method.

The galvanostat electrometer 3 is settable to predetermined voltages and currents that are switched by the timer relay 2 when the predetermined voltage or time, as the case may be in the two modes of the CCE method described above,is reached. A represents the anode, C the cathode.

The electrometer 4 is used to determine the two half-cell voltages W-R between leads 5 and 6, and C-R between leads 5 and 7. These measurements provide the predetermined upper bound voltages for the whole cell which are preset on the galvanostat electrometer. Once the upper bound voltages for a particular compound in a particular media are determined, the electrometer 4 may be omitted, as in the case of the implanted cell/control unit (galvanostat electrometer plus timer relay).

Likewise, the two-channel recorder 8 which records the half-cell potentials is optional for operation. It is useful for a visual check of the progress of the electrolysis when an operator is not present. In the case of the implanted cell/control unit, transcutaneous external leads for monitoring hook-up to a recorder may be provided, or subcutaneous induction coil type leads may be employed.

It should be understood that both or either the current and the operating voltage domain are switched. In the case of electrodes made of different materials, only the current flow needs to be reversed as each electrode operates in its own domain. In the case of both electrodes being of the same material, the controlled current (which may be constant) is usually $+80$ ma, $-80$ ma (or $+110$ ma, $-110$ ma) with the switching occurring each time the upper bound voltage is reached. In addition, the operating voltage domain of each electrode is switched from + voltage to − voltage after a predetermined time, or condition, is reached. Actual recorder traces of the FIG. 6 operations show increasingly more frequent current reversals, i.e., shorter time to reach the upper bound voltage, as electrolysis progresses. Then the operating voltage domain is reversed and the current reversal cycling continues as before. That is, the current cycles within a particular voltage domain of an electrode before the electrodes are reversed.

It should be understood that various modifications within the scope of this invention can be made by one of ordinary skill in the art without departing from the spirit thereof. For example, the method may be applied to any biological or biomedical electrolysis cell for removal of a wide variety of wastes or toxic products. We therefore wish our invention to be defined by the scope of the appended claims as broadly as the prior art will permit, and in view of this specification if need be.

We claim:

1. Biomedical electrolysis apparatus for cyclic controlled current, controlled potential electroly tic oxidation of a metabolic waste comprising in operative combination:
   (a) a continuous electrolysis cell having at least two continuously conductive electrodes including a working and a counter electrode, said cell being adapted for continuous flow therethrough, without disruption, of an aqueous media having said metabolic waste to be electrolyzed;
   (b) means for providing a controlled current, i+ to i−, between said working electrode and said counter electrode in contact with said aqueous media having said metabolic waste substance;
   (c) means for maintaining said controlled current i+ impressed on said electrodes for a period of time at least until a selected first voltage difference limit, V+, between said electrodes is achieved;
   (d) means for sensing the potential difference in said cell between said electrodes measured as voltage, V+ or V−;
   (e) means for sequentially cyclically reversing the direction of controlled current flow between said electrodes from i+ to i− in response to a predetermined voltage difference limit V+ or V− between said electrodes being sensed by said sensing means;
   (f) means for reversing the operating voltage domain of said working and counter electrodes
   (g) means for maintaining said reversed current i− impressed on said electrodes for a period of time at least until a selected second voltage difference limit, V−, between said electrodes is achieved; and
   (h) means for cyclically continuing reversals of said currents i+ and i− between said limits of said selected voltages v+ and v− to continuously electrolytically oxidize at least portions of said metabolic waste substance.

2. Biomedical electrolysis apparatus as in claim 1 which includes:
   (a) timer means for activating said voltage domain reversing means;
   (b) means for reducing the current flow to said working and counter electrodes upon said preset voltage limit, V+ or V−, being exceeded to maintain said voltage substantially at said preset voltage difference limit prior to time elapsing for said cyclic reversal.

3. A biomedical electrolysis apparatus as in claim 2 which includes:
   (a) a third electrode connected to said sensing means functioning as a reference electrode forming a first half cell in said media between said working electrode and said third electrode, and a second half cell between said counter electrode and said third electrode, said voltage differences V+ and V− being developed between said working and said reference electrodes.

4. A biomedical electrolysis apparatus as in claim 3 wherein:
   (a) said cell is adapted for in vivo implantation.

5. A biomedical electrolysis apparatus as in claim 2 wherein:
   (a) said cell is adapted for in vivo implantation.

6. A biomedical electrolysis appratus as in claim 2 wherein:
   (a) both of said working and said counter electrodes are the same, one of said electrodes operating at least in part in a negative voltage domain and the other operating at least part in a positive voltage domain.

7. A biomedical electrolysis apparatus as in claim 2 wherein:
   (a) said electrodes are selected from the group consisting of Pt-black, platinized titanium, rhodium black, palladium black, gold, rhodium, platinum and palladium electrodes.

8. A biomedical electrolysis apparatus as in claim 1 which includes:
   (a) a third electrode connected to said sensing means functioning as a reference electrode forming a first half cell in said media between said working electrode and said third electrode, and a second half cell between said counter electrode and said third electrode, said voltage differences V+ and V− being developed between said working and said reference electrodes.

9. A biomedical electrolysis apparatus as in claim 8 wherein:
   (a) said cell is adapted for in vivo implantation 10. A biomedical electrolysis apparatus as in claim 1 wherein:
    (a) said cell is adapted for in vivo implantation.

11. Biomedical electrolysis apparatus as in claim 1 wherein:
    (a) said current providing means provides at least one of said currents i+ and i− as a constant current.

12. A biomedical electrolysis apparatus as in claim 11 wherein:
    (a) said electrodes are selected from the group consisting of Pt-black, platinized titanium, rhodium black, palladium black, gold, rhodium, platinum and palladium electrodes.

13. A biomedical electrolysis apparatus as in claim 11 wherein:
   (a) both of said working and said counter electrodes are the same, one of said electrodes operating at least in part in a negative voltage domain and the other operating at least part in a positive voltage domain.

14. A biomedical electrolysis apparatus as in claim 11 which includes:
   (a) a third electrode connected to said sensing means functioning as a reference electrode forming a first half cell in said media between said working electrode and said third electrode, and a second half cell between said counter electrode and said third electrode, said voltage differences V+ and V− being developed between said working and said reference electrodes.

15. A biomedical electrolysis apparatus as in claim 14 wherein:
   (a) said electrodes are selected from the group consisting of Pt-black, platinized titanium, rhodium black, palladium black, gold, rhodium, platinum and palladium electrodes.

16. A biomedical electrolysis apparatus as in claim 15 wherein:
   (a) both of said working and said counter electrodes are the same, one of said electrodes operating at least in part in a negative voltage domain and the other operating at least in part in a positive voltage domain.

17. A biomedical electrolysis apparatus as in claim 15 wherein:
   (a) said cell is adapted for in vivo implantation.

18. A biomedical electrolysis apparatus as in claim 1 wherein:
   (a) said electrodes are selected from the group consisting of Pt-black, platinized titanium, rhodium black, palladium black, gold, rhodium, platinum and palladium electrodes.

19. A biomedical electrolysis apparatus as in claim 18 wherein:
   (a) said cell is adapted for in vivo implantation.

20. A biomedical electrolysis apparatus as in claim 1 wherein:
   (a) both of said working and said counter electrodes are the same, one of said electrodes operating at least in part in a negative voltage domain and the other operating at least part in a positive voltage domain.

* * * * *